June 11, 1963 C. H. FISCHER Plant Pat. 2,263
GLADIOLUS PLANT
Filed June 26, 1962
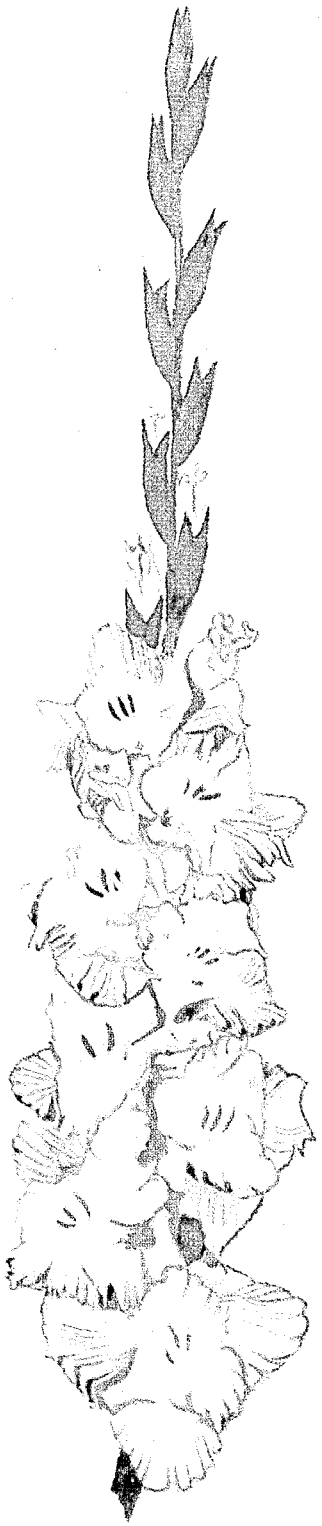
INVENTOR
Carl H. Fischer
By: Lamont Johnston
ATTORNEY United States Patent Office Plant Pat. 2,263
Patented June 11, 1963

2,263
GLADIOLUS PLANT

Carl H. Fischer, St. Charles, Minn., assignor to Selected Glads, Inc., New Albany, Ind., a corporation of Tennessee Filed June 26, 1962, Ser. No. 205,474
1 Claim. (Cl. Plt.—85)

My present invention relates to a new and improved variety of gladiolus plant and is notable particularly for its general vigor, consistency of performance, beauty of color, ruffling, and beauty of form. I have identified this new variety as section #401–57 in my breeding work.

To the best of my knowledge, this new variety is the result of a cross between the varieties Prospector and Golden Sunshine (both unpatented), Prospector being the seed parent and Golden Sunshine the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this variety, reduced in size, and is as nearly true to color as it is possible to depict. The illustration shows the extreme ruffling and beauty of color, and formal double row placement of the blooms.

In the following detailed description, color plate references are to the "Horticultural Colour Chart," by the British Colour Council. Where there are other references to color, the ordinary dictionary meanings of the terms are intended.

*The Plant*

Growth: Extremely vigorous. Bloom spike averages 60 to 65 inches in height over-all. Propagates easily.

Blooming: The variety is a rather late bloomer, coming into bloom in from 85 to 90 days in the North from large bulbs.

Stems: Straight, willowy. Diameter at base of cutting stem is ⅜ inch. Color of stem above the bulb is rose. There are brownish tints on green or reverse of spike.

Foliage: Healthy, green; leaves are broad and upright, 1¾ to 2 inches wide. Plant foliage, excluding the flower spike, is 40 inches tall.

Disease resistance: This variety has been found unusually resistant to Fusarium yellows, Sclerotina dry rot and Septoria leaf spot, to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases whereas this variety remained healthy and unaffected.

Corms: Smooth, round, plump with a slight rose tint to the husk. Flesh is Straw Yellow $604/_2$. Husk hugs corm tightly and covers it well.

*The Flower*

Spike: Tall, eighteen to twenty buds, of which seven to eight will open at once, with six buds showing color.

Bud:

*Size.*—Opening buds are 2½ to 3 inches long.

*Opening.*—Six or seven will show color at one time.

Flower:

*Arrangement.*—The flowers are formally placed in a double row on the stem and usually all face forward.

*Size.*—Individual florets are large, measuring 5 to 5¼ inches in diameter. Upper blooms are progressively smaller.

*Form.*—The florets are round and unusually broad. They are wide open, ruffled, and somewhat recurved and needle-pointed.

*Keeping qualities.*—Keeps and opens well.

Petals:

*Shape.*—Petals are broad, ruffled, recurved. Inner petals toward stem or heart of flower tend to roll back and twist.

*Size.*—Outer petals are 2 inches across; lip petal is 1¼ inches across.

*Aspects.*—Substance is very heavy. Surface is smooth, ruffled at edges.

*Fragrance.*—None.

General effect Aureolian $3/_1$. A self, except for Golden Yellow on lip petals, which are Lemon Yellow $4/_1$. Base of petal and reverse of calyx Fuchsia Purple $28/_1$. Color of calyx on reverse Fuchsia Purple $28/_3$.

Reproductive organs:

*Stamens.*—Purple.

*Pistil.*—Light yellow.

*Comparisons*

My new variety resembles Golden Sunshine (unpatented) more than any other variety, but differs from it principally as follows:

(1) My variety has a straighter stem.
(2) My variety is more intensely ruffled.
(3) My variety has greater heat tolerance.
(4) My variety folds or rolls petals toward heart of flower.

Having thus disclosed my invention, I claim:

The new and distinct variety of gladiolus plant, substantially as herein shown and described, characterized by its intense ruffling, purity of color, precision of form, and high order of beauty.

No references cited.